United States Patent
Kumar

(10) Patent No.: US 6,353,102 B1
(45) Date of Patent: Mar. 5, 2002

(54) PHOTOCHROMIC NAPHTHOPYRANS

(75) Inventor: Anil Kumar, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/466,703

(22) Filed: Dec. 17, 1999

(51) Int. Cl.[7] .................. C07D 311/78; C07D 311/92; C07D 311/96; C07D 405/02; C07D 265/28

(52) U.S. Cl. .................. 544/60; 544/150; 544/375; 546/196; 548/311.4; 548/364.4; 548/440; 548/454; 548/525; 549/43; 549/60; 549/331; 549/389

(58) Field of Search .................. 544/60, 150, 375; 549/389, 331, 60, 43; 546/196; 548/311.4, 364.4, 440, 454, 525

(56) References Cited

U.S. PATENT DOCUMENTS

| | | | |
|---|---|---|---|
| 5,274,132 A | 12/1993 | Van Gemert | 549/389 |
| 5,458,814 A | 10/1995 | Kumar et al. | 252/586 |
| 5,573,712 A | 11/1996 | Kumar et al. | 252/586 |
| 5,650,098 A | 7/1997 | Kumar et al. | 252/586 |
| 5,656,206 A | 8/1997 | Knowles | 252/586 |
| 5,658,500 A | 8/1997 | Kumar et al. | 252/586 |
| 5,658,501 A | 8/1997 | Kumar et al. | 252/586 |

FOREIGN PATENT DOCUMENTS

| | | |
|---|---|---|
| WO | WO 96/01884 | 1/1996 |
| WO | WO 98/04937 | 5/1998 |
| WO | WO 98/42693 | 10/1998 |

OTHER PUBLICATIONS

Peter Gore, "Aromatic Ketone Synthesis", Friedel–Crafts and Related Reactions, vol. III, 1964, Chap. XXXI, pp. 1–8.

Y. Ishihara et al, "Regioselective Friedel–Crafts Acylation of 1,2,3,4–Tetrahydroquinoline and Related Nitrogen Heterocycles: Effects of NH Protection Groups and Ring Size", J. Chem Soc. Perkin Trans. 1992, pp. 3401–3406.

T. Hattori et al, "Facile Construction of the 1–Phenylnapthyl Skeleton via an Ester–mediated Nucleophilic Aromatic Substitution Reaction. Applications to the Synthesis of Phenylnapthalide Lignans", J. Chem. Soc. Perkins Trans. 1995, pp. 235–241.

A. Bruggink et al, "A Study of the Copper–Catalysed Direct Arylation of β–Dicarbonyl Compounds with 2–Bromobenzoic Acids", Tetrahedron, vol. 31, pp. 2607–2619, 1975.

*Primary Examiner*—T. A. Solola
(74) *Attorney, Agent, or Firm*—Frank P. Mallak

(57) ABSTRACT

Described are novel photochromic naphtho[1,2-b]pyran compounds having certain substituents at the 2 position of the pyran ring, certain substituents at the 5 and 6 positions and optionally at the 7, 8, 9 and 10-positions of the naphtho portion of the compound. These compounds may be represented by the following graphic formula:

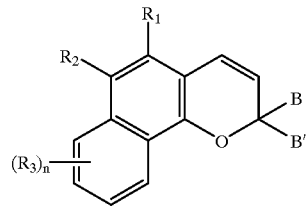

Also described are polymeric organic host materials that contain or that are coated with such compounds. Optically clear articles such as ophthalmic lenses or contact lenses that incorporate the novel naphthopyran compounds or combinations thereof with complementary photochromic compounds, e.g., certain other naphthopyrans, benzopyrans, and spiro(indoline)type compounds, are also described.

4 Claims, No Drawings

PHOTOCHROMIC NAPHTHOPYRANS

DESCRIPTION OF THE INVENTION

The present invention relates to certain novel naphthopyran compounds. More particularly, this invention relates to novel photochromic naphthopyran compounds. Still more particularly, this invention relates to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 5,458,814 discloses 2H-naphtho[1,2-b]pyrans, which are substituted at the 5- and 6-positions of the naphthopyran ring, that possess a reasonable rate of fade as well as high colorability. Said compounds exhibit activated colors ranging from yellow to red/purple.

International Patent Application Publication No. WO 98/42693 describes naphtho[1,2-b]pyrans having amino functional groups as substituents at the 7- or 9-positions of the naphthopyran ring. These compounds are disclosed as exhibiting a brown or brown/red activated color. A brown/red color is the perception by the eye of a major visible absorption in the 420–500 nm range coupled with a minor visible absorption in the 520–560 nm range.

While the activated form of a typical organic photochromic molecule absorbs in the visible region over a relatively narrow range (Van Gemert and Kish, PPG Technology Journal, Vol. 5, pg. 53–61, 1999), naphthopyrans having two absorption bands, are known.

International Patent Application Publication No. WO 98/04937 describes naphtho[1,2-b]pyrans having alkoxy groups as substituents at the 7- and 9-positions of the naphthopyran ring. The activated forms of these compounds exhibit two intense absorption bands in the visible light range.

The present invention relates to novel substituted 2H-naphtho[1,2-b]pyran compounds having substituents at the 2-position of the pyran ring, certain substituents at the 5 and 6 positions of the naphtho portion and optional substituents at the 7, 8, 9 and 10 positions of the naphtho portion of the compound. The activated forms of these compounds have unexpectedly been found to demonstrate two intense spectral bands in the visible spectrum. The absorption of one band, e.g., band "A", occurs in the 400–500 nm region, while the absorption of the second band, e.g., band "B", occurs in the 480–620 nm region. These compounds exhibit an apparent blended orange/brown to gray activated color. The use of certain individual compounds of the present invention eliminates the need for combining two or more compounds to obtain neutral colors such as gray or brown.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 2H-naphtho[1,2-b]pyrans, having two absorption bands in the activated (colored) state, an acceptable fade rate, high activated intensity and a high coloration rate may be prepared. These compounds may be described as 2H-naphtho[1,2-b]pyrans having substituents at the 2 position of the pyran ring, certain substituents at the 5 and 6 positions and optional substituents at the 7, 8, 9 and 10 positions of the naphtho portion of the compound. These compounds may be represented by the following graphic formula I in which the letters a through n on the outside of the ring structure represent the sides or faces of the naphthopyran ring, and the numbers on the inside of the ring structure represent the numbers of the ring carbon atoms or ring positions of the naphthopyran. In the definition of the substituents shown in the following graphic formula I, like symbols have the same meaning, unless stated otherwise.

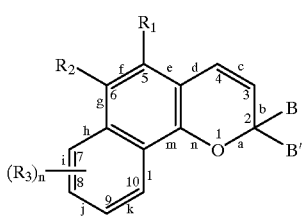

I

In graphic formula I, $R_1$ may be selected from hydroxy, $C_1-C_6$ alkoxy, aryloxy, aryl($C_1-C_6$)alkoxy, the unsubstituted, mono- or di-substituted aryl groups, phenyl or naphthyl, amino, mono($C_1-C_6$)alkylamino, di($C_1-C_6$)alkylamino, phenylamino, mono- or di-($C_1-C_6$)alkyl substituted phenylamino, mono- or di-($C_1-C_6$)alkoxy substituted phenylamino, diphenylamino, mono- or di-($C_1-C_6$)alkyl substituted diphenylamino, mono- or di-($C_1-C_6$)alkoxy substituted diphenylamino, morpholino, thiomorpholino, piperazino, piperidino, dicyclohexylamino, pyrrolidyl, or the group —OCH($R_4$)Z, said aryl substituents of $R_1$ being selected from the group consisting of $C_1-C_6$ alkyl, $C_1-C_6$ alkoxy, $C_3-C_6$ cycloalkyl, phenyl($C_1-C_6$)alkyl, amino, mono($C_1-C_6$)alkylamino, di($C_1-C_6$)alkylamino, dicyclohexylamino, diphenylamino, piperidino, morpholino, pyrrolidyl, bromo, chloro, fluoro, phenyl and naphthyl; Z is —CN, —$CF_3$, chloro, fluoro or —C(O)$R_8$; $R_4$ is hydrogen or $C_1-C_6$ alkyl; and $R_8$ is hydrogen, $C_1-C_6$ alkyl or $C_1-C_6$ alkoxy.

Preferably, $R_1$ is selected from hydroxy, $C_1-C_4$ alkoxy, the unsubstituted, mono- or di-substituted aryl groups, phenyl or naphthyl, amino, mono($C_1-C_4$)alkylamino, di($C_1-C_4$)alkylamino, phenylamino, mono- or di-($C_1-C_4$)alkyl substituted phenylamino, mono- or di-($C_1-C_4$)alkoxy substituted phenylamino, diphenylamino, mono- or di-($C_1-C_4$)alkyl substituted diphenylamino, mono- or di-($C_1-C_4$)alkoxy substituted diphenylamino, morpholino, piperidino, dicyclohexylamino, pyrrolidyl, or the group —OCH($R_4$)Z, said aryl substituents being selected from the group consisting of $C_1-C_4$ alkyl, $C_1-C_4$ alkoxy, $C_3-C_5$ cycloalkyl, phenyl($C_1-C_4$)alkyl, amino, mono($C_1-C_4$)alkylamino, di($C_1-C_4$)alkylamino, dicyclohexylamino, diphenylamino, piperidino, morpholino, pyrrolidyl, bromo, chloro, fluoro, phenyl and naphthyl; Z is —CN, chloro, fluoro or —C(O)$R_8$; $R_4$ is hydrogen or $C_1-C_4$ alkyl; and $R_8$ is hydrogen, $C_1-C_4$ alkyl or $C_1-C_4$ alkoxy.

More preferably, $R_1$ is selected from hydroxy, $C_1-C_3$ alkyl, phenyl, mono- or di-substituted phenyl, amino, mono($C_1-C_3$)alkylamino, di($C_1-C_3$)alkylamino, morpholino, piperidino, pyrrolidyl, or the group —OCH($R_4$)Z, said phenyl substituents being selected from the group consisting of $C_1-C_3$ alkyl, $C_1-C_3$ alkoxy, phenyl($C_1-C_3$) alkyl, amino, mono($C_1-C_3$)alkylamino, di($C_1-C_3$) alkylamino, piperidino, morpholino, pyrrolidyl, bromo, chloro, fluoro, phenyl and naphthyl; Z is chloro, fluoro or —C(O)$R_8$; $R_4$ is hydrogen or $C_1-C_3$ alkyl; and $R_8$ is hydrogen, $C_1-C_3$ alkyl or $C_1-C_3$ alkoxy.

$R_2$ in graphic formula I, may be the group, —C(O)W, wherein: W is hydrogen, hydroxy, $C_1-C_6$ alkyl, the unsubstituted, mono- or di-substituted aryl groups, phenyl or naphthyl, the group, —OCH($R_4$)Z, —O$R_5$, or —N($R_6$)($R_7$) or an unsubstituted, mono-substituted or di-substituted aromatic and/or non-aromatic heterocyclic ring selected from the group consisting of 1-indolinyl, morpholino, thiomorpholino, piperidino, 1-pyrrolidyl, 1-imidazolidyl, 2-imidazolin-1-yl, pyrazolidyl, pyrazolinyl and 1-piperazinyl; $R_5$ is $C_1-C_6$ alkyl, allyl, phenyl($C_1-C_3$)alkyl, mono($C_1-C_6$)alkyl substituted phenyl($C_1-C_3$)alkyl, mono ($C_1-C_6$)alkoxy substituted phenyl($C_1-C_3$)alkyl, ($C_1-C_6$) alkoxy($C_2-C_4$)alkyl, $C_1-C_6$ haloalkyl, or the unsubstituted, mono- or di-substituted aryl groups, phenyl or naphthyl, said halo substituent being chloro or fluoro; and $R_6$ and $R_7$ are each selected from the group consisting of hydrogen, $C_1-C_6$ alkyl, $C_5-C_7$ cycloalkyl, phenyl, mono-substituted phenyl and di-substituted phenyl, each of said aforedescribed phenyl, aryl, naphthyl and heterocyclic ring substituents of $R_2$ being $C_1-C_6$ alkyl or $C_1-C_6$ alkoxy;

Preferably, $R_2$ is selected from the group, —C(O)W, wherein: W is hydrogen, hydroxy, $C_1-C_4$ alkyl, the unsubstituted, mono- or di-substituted aryl groups, phenyl or naphthyl, the group, —OCH($R_4$)Z, —O$R_5$, or —N($R_6$)($R_7$) or an unsubstituted, mono-substituted or di-substituted heterocyclic ring selected from the group consisting of 1-indolinyl, morpholino, thiomorpholino, piperidino, 1-pyrrolidyl, 1-imidazolidyl, 2-imidazolin-1-yl, pyrazolidyl, pyrazolinyl and 1-piperazinyl; $R_5$ is $C_1-C_4$ alkyl, allyl, phenyl($C_1-C_2$)alkyl, mono($C_1-C_4$)alkyl substituted phenyl ($C_1-C_2$)alkyl, mono($C_1-C_4$)alkoxy substituted phenyl ($C_1-C_2$)alkyl, ($C_1-C_4$)alkoxy($C_2-C_3$)alkyl, $C_1-C_4$ haloalkyl, or the unsubstituted, mono- or di-substituted aryl groups, phenyl or naphthyl, said halo substituent being chloro or fluoro; and $R_6$ and $R_7$ are each selected from the group consisting of hydrogen, $C_1-C_4$ alkyl, $c_5-C_6$ cycloalkyl, phenyl, mono-substituted phenyl and di-substituted phenyl, each of said aforedescribed phenyl, aryl, naphthyl and heterocyclic ring substituents being $C_1-C_4$ alkyl or $C_1-C_4$ alkoxy.

More preferably, $R_2$ is selected from the group, —C(O)W, wherein: W is hydrogen, hydroxy, $C_1-C_3$ alkyl, phenyl, mono- or di-substituted phenyl, the group, —OCH($R_4$)Z, —O$R_5$, or —N($R_6$)($R_7$) or an unsubstituted, mono-substituted or di-substituted heterocyclic ring selected from the group consisting of 1-indolinyl, morpholino, piperidino, and 1-pyrrolidyl; $R_5$ is $C_1-C_3$ alkyl, allyl, phenyl($C_1-C_2$) alkyl, mono($C_1-C_3$)alkyl substituted phenyl($C_1-C_2$)alkyl, mono($C_1-C_3$)alkoxy substituted phenyl($C_1-C_2$)alkyl, ($C_1-C_3$)alkoxy($C_2-C_3$)alkyl, $C_1-C_3$ haloalkyl, or phenyl, mono- or di-substituted phenyl, said halo substituent being chloro or fluoro; and $R_6$ and $R_7$ are each selected from the group consisting of hydrogen, $C_1-C_3$ alkyl, phenyl, mono-substituted phenyl and di-substituted phenyl, each of said aforedescribed phenyl and heterocyclic ring substituents being $C_1-C_3$ alkyl or $C_1-C_3$ alkoxy.

Each $R_3$ in graphic formula I, may be selected from $C_1-C_6$ alkyl, $C_1-C_6$ alkoxy, $C_3-C_7$ cycloalkyl, phenyl, mono- or di-substituted phenyl, said phenyl substituents being $C_1-C_6$ alkyl or $C_1-C_6$ alkoxy and n is selected from the integers 0, 1, 2 or 3. Preferably, each $R_3$ is selected from $C_1-C_4$ alkyl, $C_1-C_4$ alkoxy, $C_3-C_6$ cycloalkyl, phenyl, mono- or di-substituted phenyl, said phenyl substituents being $C_1-C_4$ alkyl or $C_1-C_4$ alkoxy and n is selected from the integers 0, 1 or 2. More preferably, $R_3$ is selected from $C_1-C_3$ alkyl, $C_1-C_3$ alkoxy, $C_3-C_5$ cycloalkyl, phenyl, mono- or di-substituted phenyl, said phenyl substituents being $C_1-C_3$ alkyl or $C_1-C_3$ alkoxy and n is selected from the integers 0 or 1.

B and B' in graphic formula I may each be selected from the group consisting of:

(i) the unsubstituted, mono-, di-, and tri-substituted aryl groups, phenyl and naphthyl;

(ii) the unsubstituted, mono- and di-substituted aromatic heterocyclic groups, pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, and fluorenyl, each of said aryl and aromatic heterocyclic substituents in parts (i) and (ii) being selected from the group consisting of hydroxy, aryl, mono($C_1-C_6$)alkoxyaryl, di($C_1-C_6$)alkoxyaryl, mono($C_1-C_6$)alkylaryl, di($C_1-C_6$)alkylaryl, chloroaryl, fluoroaryl, $C_3-C_7$ cycloalkylaryl, $C_3-C_7$ cycloalkyl, $C_3-C_7$ cycloalkyloxy, $C_3-C_7$ cycloalkyloxy($C_1-C_6$) alkyl, $C_3-C_7$ cycloalkyloxy($C_1-C_6$)alkoxy, aryl ($C_1-C_6$)alkyl, aryl($C_1-C_6$)alkoxy, aryloxy, aryloxy ($C_1-C_6$)alkyl, aryloxy($C_1-C_6$)alkoxy, mono- and di-($C_1-C_6$)alkylaryl($C_1-C_6$)alkyl, mono- and di-($C_1-C_6$) alkoxyaryl($C_1-C_6$)alkyl, mono- and di-($C_1-C_6$) alkylaryl($C_1-C_6$)alkoxy, mono- and di-($C_1-C_6$) alkoxyaryl($C_1-C_6$)alkoxy, amino, mono($C_1-C_6$) alkylamino, di($C_1-C_6$)alkylamino, diarylamino, piperazino, N-($C_1-C_6$)alkylpiperazino, N-arylpiperazino, aziridino, indolino, piperidino, morpholino, thiomorpholino, tetrahydroquinolino, tetrahydroisoquinolino, pyrrolidyl, $C_1-C_6$ alkyl, $C_1-C_6$ chloroalkyl, $C_1-C_6$ fluoroalkyl, $C_1-C_6$ alkoxy, mono ($C_1-C_6$)alkoxy($C_1-C_4$)alkyl, acryloxy, methacryloxy, bromo, chloro and fluoro, said term aryl, as used in this part (ii) when referring to an aryl substituent, refers to phenyl or naphthyl;

(iii) the unsubstituted or mono-substituted groups, pyrazolyl, imidazolyl, indolyl, pyridyl, pyrazolinyl, imidazolinyl, pyrrolinyl, phenothiazinyl, phenoxazinyl, phenazinyl, or acridinyl each of said substituents being selected from the group consisting of $C_1-C_6$ alkyl, $C_1-C_4$ alkoxy, phenyl, fluoro, chloro and bromo;

(iv) para-substituted phenyl wherein the para substituent is the linking group, —(CH$_2$)$_t$— or —O—(CH$_2$)$_t$—, wherein t is the integer 1, 2, 3, 4, 5 or 6, said linking group being connected to an aryl group, e.g. phenyl or naphthyl, which is a segment of another photochromic naphthopyran, such as naphtho[2,1-b]pyran or naphtho [1,2-b]pyran;

(v) the groups represented by the following graphic formulae:

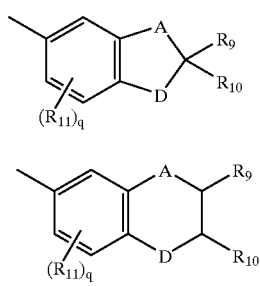

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_1$l is $C_1$–$C_6$ alkyl, $C_1$–$C_6$ alkoxy, hydroxy, chloro or fluoro; $R_9$ and $R_{10}$ are each hydrogen or $C_1$–$C_6$ alkyl; and q is the integer 0, 1, or 2;

(vi) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl ($C_3$–$C_6$)-cycloalkyl, chloro($C_3$–$C_6$)cycloalkyl, fluoro ($C_3$–$C_6$)cycloalkyl and $C_4$–$C_{12}$ bicycloalkyl; and (vii) the group represented by the following graphic formula:

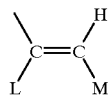

wherein L in graphic formula IIC may be hydrogen or $C_1$–$C_4$ alkyl and M in graphic formula IIC may be selected from the unsubstituted, mono-, and di-substituted members of the group consisting of naphthyl, phenyl, furanyl, and thienyl, each of said group substituents in this part (vii) being $C_1$–$C_4$ alkyl, $C_1$–$C_4$ alkoxy, fluoro, or chloro.

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

Preferably, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents in parts (i) and (ii) being selected from the group consisting of hydroxy, phenyl($C_1$–$C_4$)alkyl, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$) alkyl, fluoro and chloro; (iii) the groups represented by the graphic formulae IIA and IIB, wherein A is carbon and D is oxygen, $R_{11}$ is $C_1$–$C_3$ alkyl or $C_1$–$C_3$ alkoxy, $R_9$ and Rlo are each hydrogen or $C_1$–$C_3$ alkyl; and q is the integer 0 or 1; (iv) $C_1$–$C_4$ alkyl; and (v) the group represented by the graphic formula IIC wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

More preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, phenyl($C_1$–$C_3$)alkyl, $C_1$–$C_3$ alkyl, $C_1$–$C_3$ alkoxy, fluoro and chloro; and (iii) the group represented by graphic formula IIA, wherein A is carbon and D is oxygen, $R_{11}$ is $C_1$–$C_3$ alkyl or $C_1$–$C_3$ alkoxy, $R_9$ and $R_{10}$ are each hydrogen or $C_1$–$C_3$ alkyl, and q is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula I, which have the substituents $R_1$–$R_3$, and B and B' described hereinbefore, may be prepared by the following Reactions A through G.

Compounds represented by graphic formula V, or VA are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles:

Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B). R and R' represent possible substituents, as described hereinbefore with respect to graphic formula I.

REACTION A

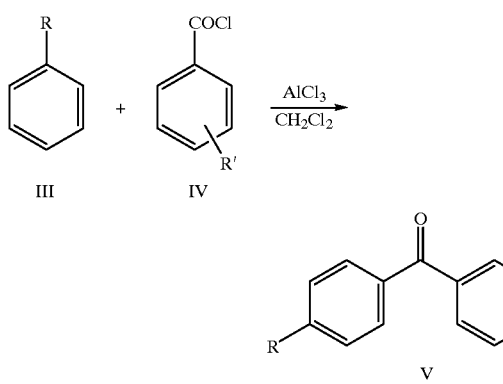

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

REACTION B

In Reaction C, a substituted 2-bromoacetophenone represented by graphic formula VII is condensed with diethyl malonate represented by graphic formula VIII in the presence of copper(I) bromide and sodium hydride to produce ethyl-1,3-dihydroxy-4-naphthoate represented by graphic formula IX. See Bruggink, A. and McKillop, A., *Tetrahedron*, Vol. 31, pp 2607–2619, 1975. Substituting different reagents for diethyl malonate will alter the substituent found at the 3-position of naphthol, i.e., $R_1$. For example ethyl-3-phenyl-1-hydroxy-4-naphthoate can be prepared by using ethyl benzoylacetate instead of diethyl malonate to result in $R_1$ being a phenyl substituent.

REACTION C

In Reaction D, a substituted ethyl-1,3-dihydroxy-4-naphthoate represented by graphic formula IX is coupled with the propargyl alcohol represented by graphic formula VI in the presence of a catalytic amount of p-toluenesulfonic acid (p-TSA) to produce the desired naphthopyran represented by graphic formula X.

REACTION D

In Reaction E, the naphthopyran represented by graphic formula X is methylated with methyl iodide in the presence of potassium carbonate and acetone to form the naphthopyran represented by graphic formula XI.

REACTION E

In Reaction F, the naphthopyran of graphic formula X can be further derivatized by reaction with bromomagnesium morpholinamide to form the compound represented by graphic formula XII.

phenyl Grignard or morpholino Grignard results in the formation of the compounds represented by graphic formulae XIII and XIV, respectively.

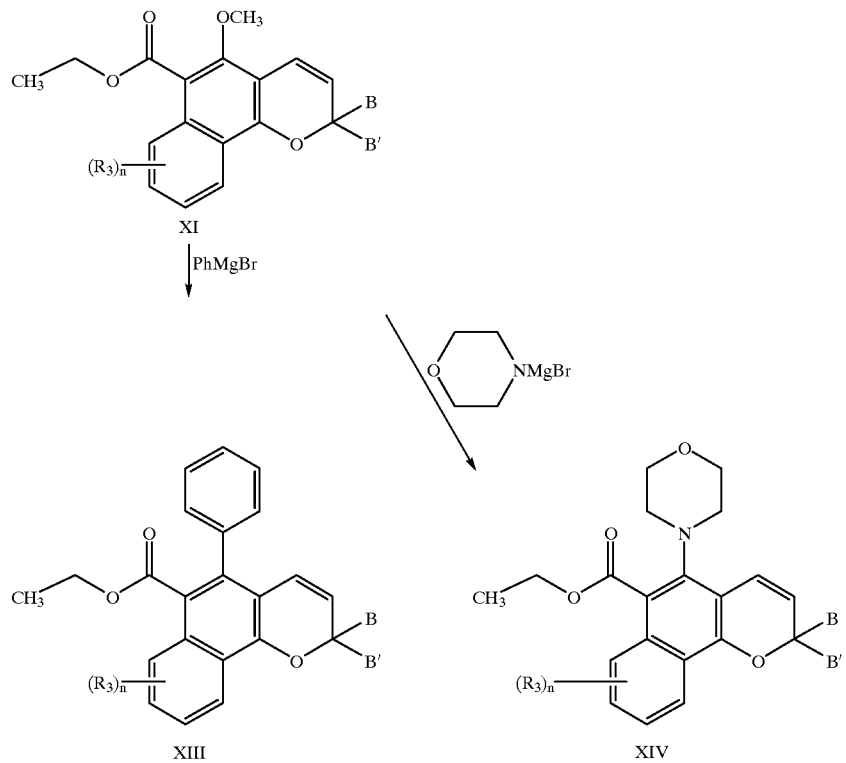

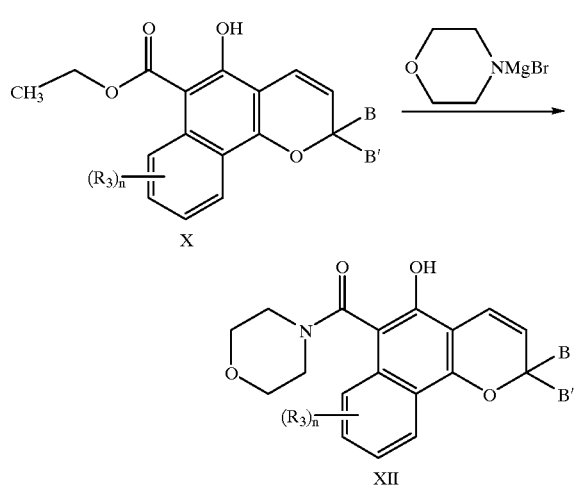

In Reaction G, the naphthopyran of graphic formula XI is derivatized by reaction with a Grignard reagent and undergoes an ester-mediated nucleophilic aromatic substitution. See Hattori, T.; Tanaka, H.; Okaishi, Y. and Miyano, S., *J. Chem. Soc. Perkin Trans. I*, pp 235–241, (1995). The reaction of the naphthopyran of graphic formula XI with Compounds represented by graphic formula I may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. The substituted naphtho[1,2-b]pyrans represented by graphic formula I exhibit color changes from colorless to colors ranging from orange/brown to gray.

Examples of the contemplated naphthopyran compounds within the scope of the invention include the following:

(a) 2,2-phenyl-5-hydroxy-6-carboethoxy-2H-naphtho[1,2-b]pyran;
(b) 2,2-phenyl-5-methoxy-6-carboethoxy-2H-naphtho[1,2-b]pyran;
(c) 2,2-phenyl-5-hydroxy-6-morpholinocarbonyl-2H-naphtho[1,2-b]pyran;
(d) 2,2-phenyl-5-morpholino-6-carboethoxy-2H-naphtho[1,2-b]pyran;
(e) 2,2,5-triphenyl-6-carboethoxy-2H-naphtho[1,2-b]pyran;
(f) 2-(4-methoxyphenyl)-2-(4-morpholinophenyl)-5-hydroxy-6-carboethoxy-2H-naphtho[1,2-b]pyran;

(g) 2,2-diphenyl-5-hydroxy-6-carbomethoxy-9-methoxy-2H-naphtho[1,2-b]pyran;

(h) 2-(4-methoxyphenyl)-2-phenyl-5-morpholino-6-carbomethoxy-9-methoxy-2H-naphtho[1,2-b]pyran; and (i) 2-(4-methoxyphenyl)-2-phenyl-5-morpholino-6-carbomethoxy-9-methyl-2H-naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in or applied to (in an appropriate carrier, such as a solvent or organic polymer) a polymeric organic host material used to prepare photochromic articles and which color when activated to an appropriate hue.

Other than where otherwise indicated, all values such as those expressing wavelengths, quantities of ingredients or reaction conditions, used herein are to be understood as modified in all instances by the term "about".

Examples of complementary organic photochromic compounds include other naphthopyrans, chromenes, oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, indenonaphthopyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,931; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432, 5,698,141, 5,723,072, 5,744,070, 5,783,116 and 5,811,034.

Spiro(indoline)pyrans are also described in the text, *Techniques in Chemistry*, Volume III, "Photochromism", Chapter 3, Glenn H. Brown, Editor, John Wiley and Sons, Inc., New York, 1971.

The complementary organic photochromic materials may also include polymerizable photochromic compounds, such as those disclosed in U.S. Pat. Nos. 4,719,296; 5,166,345; 5,236,958; 5,252,742; 5,359,035; and 5,488,119.

Other complementary photochromic substances contemplated are photochromic metal-dithizonates, e.g. mercury dithizonates which are described in, for example, U.S. Pat. No. 3,361,706, and fulgides and fulgimides, e.g. the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 2.0, e.g., from 0.2 to 1.0, milligrams per square centimeter of surface to which the photochromic substance (s) is incorporated or applied. The amount of photochromic material incorporated into a coating composition may range from 0.1 to 40 weight percent, based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form.

Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39,- and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear coatings and polymerizates, i.e., materials suitable for optical applications, such as for example lenses, i.e., plano, ophthalmic and contact lenses. Optically clear polymerizates may have a refractive index that may range from about 1.48 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52, which disclosure is incorporated herein by reference. Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631, both disclosures of which are incorporated herein by reference.

The present invention is more particularly described in the following examples which are intended as illustrative only, since numerous modifications and variations therein will be apparent to those skilled in the art.

EXAMPLE 1

Step 1

Sodium hydride (4 grams) was slowly added to a reaction flask containing a mixture of 2-bromoacetophenone (10 grams or 0.05 moles), diethyl malonate, 60 milliliters (mL) and of copper(I) bromide (0.4 gram). The resulting mixture was stirred and heated at 80° C. for 5 hours. The mixture was cooled, poured into 500 mL of water and the mixture was extracted with methylene chloride. The resulting aqueous layer was filtered to remove inorganic solids and acidified with concentrated HCl. The acidic mixture was extracted with diethyl ether. The organic layer was separated, washed with water, dried over anhydrous sodium sulfate and concentrated.

The concentrate rapidly turned into solid which was recrystallized from a methylene chloride/hexane mixture (1:1). The amount of ethyl 2,4-dihydroxy-1-naphthoate product recovered was 4.0 grams. The product had a melting point of 133–134° C.

Step 2

The product from Step 1 (2 grams or 0.0086 moles) and 1,1-diphenyl-2-propyn-1-ol (2 grams or 0.0096 moles) were added to a reaction flask containing 100 mL of chloroform and stirred at room temperature. p-Toluenesulfonic acid, [100 milligrams (mg)], was added to the mixture, which was stirred further for 8 hours. The reaction was monitored by TLC and HPLC. The solvent was evaporated and the resulting oily residue was crystallized from diethyl ether. The solid product was suction filtered, washed with hexane and air dried. The recovered product, 2.2 grams, had a melting point of 154–155° C. A nuclear magnetic resonance (NMR) spectrum showed the product to have a structure consistent with 2,2-phenyl-5-hydroxy-6-carboethoxy-2H-naphtho[1,2-b]pyran.

EXAMPLE 2

2,2-Phenyl-5-hydroxy-6-carboethoxy-2H-naphtho[1,2-b] pyran (1 gram) from Example 1, anhydrous potassium carbonate powder (2 grams) and methyl iodide (2 mL) were added to a reaction flask containing 50 mL of anhydrous acetone and refluxed under inert atmosphere for six hours. The solvent was evaporated and 100 mL each of water and chloroform were added. The resulting mixture was stirred for 30 minutes. The organic layer was separated, washed with water, dried over anhydrous sodium sulfate and concentrated. The resulting oily concentrate was crystallized from diethyl ether. The solid product was suction filtered, washed with hexane and air dried. The recovered product, 0.9 gram, had a melting point of 125–126° C. A nuclear magnetic resonance (NMR) spectrum showed the product to have a structure consistent with 2,2-phenyl-5-methoxy-6-carboethoxy-2H-naphtho[1,2-b]pyran.

EXAMPLE 3

Ethyl magnesium chloride (8 ml of a 3 molar solution in hexane) was added to a flask containing morpholine (3 mL) and 50 mL of anhydrous tetrahydrofuran and stirred for an hour. 2,2-Phenyl-5-hydroxy-6-carboethoxy-2H-naphtho[1,2-b]pyran from Example 1 (0.50 gram) in 5 ml of anhydrous tetrahydrofuran was added to the reaction mixture and stirred at room temperature for 2 hours. 5% HCl aqueous solution (100 mL) was added and the resulting mixture was extracted with three 25 mL portions of diethyl ether. The organic extracts were combined and washed with distilled water and dried over anhydrous magnesium sulfate. Evaporation of solvent resulted in an oily product. The oily concentrate was crystallized from diethyl ether. The resulting solid product was suction filtered, washed with hexane and air dried. The recovered product, 0.30 gram, had a melting point of 195–196° C. A nuclear magnetic resonance (NMR) spectrum showed the product to have a structure consistent with 2,2-phenyl-5-hydroxy-6-morpholinocarbonyl-2H-naphtho[1,2-b]pyran.

EXAMPLE 4

Ethyl magnesium chloride (8 mL of a 3 molar solution in hexane) was added to a flask containing 3 mL morpholine and 50 mL of anhydrous tetrahydrofuran and stirred for an hour. 2,2-Phenyl-5-methoxy-6-carboethoxy-2H-naphtho[1,2-b]pyran from Example 2 (1.0 gram) in 5 mL of anhydrous tetrahydrofuran was added to the reaction mixture and stirred at room temperature for 2 hours. 5% HCl aqueous solution (100 mL) was added and the resulting mixture was extracted with three 25 mL portions of diethyl ether. The organic extracts were combined and washed with distilled water and dried over anhydrous magnesium sulfate. Evaporation of solvent resulted in an oily product. The oily concentrate was crystallized from diethyl ether. The resulting solid product was suction filtered, washed with hexane and air dried. The recovered product, 0.9 gram, had a melting point of 204–205° C. A nuclear magnetic resonance (NMR) spectrum showed the product to have a structure consistent with 2,2-phenyl-5-morpholino-6-carboethoxy-2H-naphtho[1,2-b]pyran.

EXAMPLE 5

Phenyl magnesium bromide (10 mL of a 2 molar solution) was slowly added to a reaction flask containing 2,2-diphenyl-5-methoxy-6-carboethoxy-2H-naphtho[1,2-b] pyran from Example 2 (0.5 gram) and 50 mL of anhydrous tetrahydrofuran and stirred for two hours. 5% HCl aqueous solution (100 mL) was added and the resulting mixture was extracted with three 25 mL portions of diethyl ether. The organic extracts were combined and washed with distilled water and dried over anhydrous magnesium sulfate. Evaporation of solvent resulted in an oily product. The oily concentrate was crystallized from diethyl ether. The resulting solid product was suction filtered, washed with hexane and air dried. The recovered product, 0.4 gram, had a melting point of 183–184° C. A nuclear magnetic resonance (NMR) spectrum showed the product to have a structure consistent with 2,2,5-triphenyl-6-carboethoxy-2H-naphtho[1,2-b]pyran.

EXAMPLE 6

The product from Step 1 (1 gram or 0.0043 moles) of Example 1 and 1-(4-methoxyphenyl)-1-(4-morpholinophenyl)-2-propyn-1-ol (1.5 grams or 0.0046 moles) were added to a reaction flask containing 50 mL of chloroform and stirred at room temperature. p-Toluenesulfonic acid (100 mg) was added to the mixture, which was stirred further for 8 hours.

Evaporation of solvent resulted in an oily product. The oily concentrate was crystallized from diethyl ether. The solid product was suction filtered, washed with hexane and air dried. The recovered product, 1.3 grams, had a melting point of 137–138° C. A nuclear magnetic resonance (NMR) spectrum showed the product to have a structure consistent with 2-(4-methoxyphenyl)-2-(4-morpholinophenyl)-5-hydroxy-6-carboethoxy-2H-naphtho[1,2-b]pyran.

EXAMPLE 7

Part A

Testing was done with the photochromic compounds described in Examples 1 through 6 in the following manner. A quantity of photochromic compound calculated to yield a $1.5 \times 10^3$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 300 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.11 to 0.14 milliwatts per square centimeter (mW/cm$^2$) for the samples of Examples 2, 4, 5 and 6. The power output for samples of Examples 1 and 3 ranged from 0.17 to 0.19 mW/cm$^2$. Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 300) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: ΔOD=log(100/% Ta), where % Ta is the percent transmittance in the activated state and the logarithm is to the base 10.

The optical properties of the photochromic compounds in the test squares are reported in Table 1. The saturation optical density (ΔOD@ Saturation) was measured over 15 minutes of UV exposure. The lambda max (Vis) is the wavelength in the visible spectrum at which the maximum absorption of the activated (colored) form of the photochromic compound in a test square occurs. The lambda max (vis) wavelengths reported in Table 1 were determined by testing the photochromic test square polymerizates of Part A in a Varian Cary 3 uv-visible spectrophotometer. The bleach rate (T ½) is the time interval in seconds for the absorbance of the activated form of the photochromic compound in the test squares to read one half the highest absorbance at room temperature (72° F., 22.2° C.) after removal of the source of activating light.

Each of the compounds of the Examples exhibited dual peak absorptions in the visible spectrum (lambda max visible) in distinct color regions. For each lambda max visible, the corresponding optical density (ΔOD at saturation), for the compounds of the Examples are tabulated in Table 1 for the two bands (A and B) of peak absorption for each compound. Table 1 also includes the bleach rate (T ½) for each of the compounds as measured at bands A and B.

TABLE 1

| Compound Example | ΔOD @ Saturation | Bleach Rate T 1/2 sec. | λ MAX (Vis) (nm) |
|---|---|---|---|
| 1 (Band A) | 0.18 | 29 | 410 |
| 1 (Band B) | 0.08 | 28 | 528 |
| 2 (Band A) | 0.10 | 54 | 406 |
| 2 (Band B) | 0.14 | 60 | 499 |
| 3 (Band A) | 0.46 | 96 | 406 |
| 3 (Band B) | 0.18 | 137 | 531 |
| 4 (Band A) | 0.11 | 37 | 424 |
| 4 (Band B) | 0.05 | 36 | 530 |
| 5 (Band A) | 0.10 | 47 | 406 |
| 5 (Band B) | 0.15 | 49 | 487 |
| 6 (Band A) | 0.02 | 147 | 492 |
| 6 (Band B) | 0.03 | 120 | 596 |

The data presented in Table 1 show that each tested compound of the present invention has two absorption peaks in the visible spectrum. The Example compounds also demonstrate an acceptable bleach rate, i.e., fade rate.

This data demonstrates that a single compound of the present invention exhibits a blended activated hue. In the preparation of photochromic articles with a desired activated hue, a combination of complementary photochromic compounds each having an activated visible absorption maximum may be used. The activated visible absorption maxima of the various compounds are thereby blended to achieve the desired activated color. By employing a compound of the present invention having two activated visible absorption maxima, fewer distinct compounds are required to achieve a blend of activated visible absorption maxima to produce the desired activated hue, e.g. neutral color.

The present invention has been described with reference to specific details of particular embodiments thereof. It is not intended that such details be regarded as limitations upon the scope of the invention except insofar as to the extent that they are included in the accompanying claims.

I claim:

1. A naphthopyran compound represented by the following graphic formula:

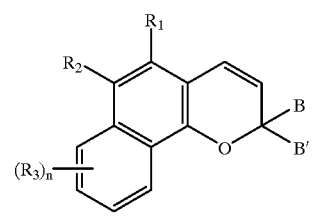

wherein,
(a) $R_1$ is selected from hydroxy, $C_1$–$C_6$ alkoxy, aryloxy, aryl($C_1$–$C_6$)alkoxy; the unsubstituted, mono- or di-substituted aryl groups, phenyl or naphthyl; amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$) alkyl substituted diphenylamino, mono- or di-($C_1$–$C_6$) alkoxy substituted diphenylamino, morpholino, thiomorpholino, piperazino, piperidino, dicyclohexylamino, pyrrolidyl; or the group —OCH($R_4$)Z; said aryl substituents being selected from the group consisting of $C_1$–$C_6$ alkyl, $C_1$–$C_6$ alkoxy, $C_3$–$C_6$ cycloalkyl, phenyl($C_1$–$C_6$)alkyl, amino, mono($C_1$–$C_6$) alkylamino, di($C_1$–$C_6$)alkylamino, dicyclohexylamino, diphenylamino, piperidino, morpholino, pyrrolidyl, bromo, chloro, fluoro, phenyl and naphthyl; Z is —CN, —$CF_3$, chloro, fluoro or —C(O)$R_8$; $R_4$ is hydrogen or $C_1$–$C_6$ alkyl; and $R_8$ is hydrogen, $C_1$–$C_6$ alkyl or $C_1$–$C_6$ alkoxy;

(b) $R_2$ is the group, —C(O)W, wherein: W is hydrogen, hydroxy, $C_1$–$C_6$ alkyl; the unsubstituted, mono- or di-substituted aryl groups, phenyl or naphthyl; the group —OCH($R_4$)Z, —O$R_5$, or —N($R_6$)($R_7$); or an unsubstituted, mono-substituted or di-substituted heterocyclic ring selected from the group consisting of 1-indolinyl, morpholino, thiomorpholino, piperidino, 1-pyrrolidyl, 1-imidazolidyl, 2-imidazolin-1-yl, pyrazolidyl, pyrazolinyl and 1-piperazinyl; $R_5$ is $C_1$–$C_6$ alkyl, allyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy ($C_2$–$C_4$)alkyl, $C_1$–$C_6$ haloalkyl; or the unsubstituted, mono- or di-substituted aryl groups, phenyl or naphthyl; said halo substituent being chloro or fluoro; and $R_6$ and $R_7$ are each selected from the group consisting of hydrogen, $C_1$–$C_6$ alkyl, $C_5$–$C_7$ cycloalkyl, phenyl, mono-substituted phenyl and di-substituted phenyl; each of said phenyl, aryl, naphthyl and heterocyclic ring substituents being $C_1$–$C_6$ alkyl or $C_1$–$C_6$ alkoxy;

(c) each $R_3$ is $C_1$–$C_6$ alkyl, $C_1$–$C_6$ alkoxy, $C_3$–$C_7$ cycloalkyl, phenyl, mono- or di-substituted phenyl; said phenyl substituents being $C_1$–$C_6$ alkyl or $C_1$–$C_6$ alkoxy, and n is selected from the integers 0, 1, 2 or 3; and (d) B and B' are each selected from the group consisting of:
  (i) the unsubstituted, mono-, di-, and tri-substituted aryl groups, phenyl and naphthyl;
  (ii) the unsubstituted, mono- and di-substituted heteroaromatic groups, pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, and fluorenyl; each of said aryl and heteroaromatic substituents in (d) (i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$) alkoxy, aryloxy, aryloxy($C_1$–$C_6$)alkyl, aryloxy ($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl ($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro; said aryl group being phenyl or naphthyl;

(iii) the unsubstituted or mono-substituted groups diarylamino, pyrazolyl, imidazolyl, indolyl, pyridyl, pyrazolinyl, imidazolinyl, pyrrolinyl, phenothiazinyl, phenoxazinyl, phenazinyl, or acridinyl; said aryl group being phenyl or naphthyl and each of said substituents being selected from the group consisting of $C_1$–$C_6$ alkyl, $C_1$–$C_4$ alkoxy, phenyl, fluoro, chloro and bromo;

(iv) para-substituted phenyl wherein said para substituent is the linking group, —($CH_2$)$_t$— or —O—($CH_2$)$_t$—; wherein t is the integer 1, 2, 3, 4, 5 or 6; said linking group being connected to an aryl group, which is a segment of another photochromic naphthopyran;

(v) the groups represented by the following graphic formulae:

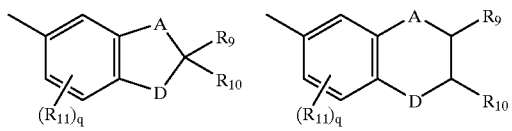

wherein A is carbon or oxygen and D is oxygen or substituted nitrogen, provided that when D is substituted nitrogen, A is carbon; said nitrogen substituents being selected from the group consisting of hydrogen, $C_1$–$C_6$ alkyl, and $C_2$–$C_6$ acyl; each $R_{11}$ is $C_1$–$C_6$ alkyl, $C_1$–$C_6$ alkoxy, hydroxy, chloro or fluoro; $R_9$ and $R_{10}$ are each hydrogen or $C_1$–$C_6$ alkyl; and q is the integer 0, 1, or 2;

(vi) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)-cycloalkyl, chloro ($C_3$–$C_6$)cycloalkyl, fluoro($C_3$–$C_6$)cycloalkyl and $C_4$–$C_{12}$ bicycloalkyl; and (vii) the group represented by the following graphic formula:

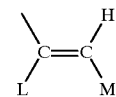

wherein L is hydrogen or $C_1$–$C_4$ alkyl and M is selected from the unsubstituted, mono-, and di-substituted members of the group consisting of naphthyl, phenyl, furanyl, and thienyl; each of said group substituents being $C_1$–$C_4$ alkyl, $C_1$–$C_4$ alkoxy, fluoro, or chloro; or (e) B and B' taken together form fluoren-9-ylidene, mono-, or di-substituted fluoren-9-ylidene; or a member selected from the group consisting of saturated $C_3$–$C_{12}$ spiro-monocyclic hydrocarbon rings; saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1, wherein
(a) $R_1$ is selected from hydroxy, $C_1$–$C_4$ alkoxy; the unsubstituted, mono- or di-substituted aryl groups, phenyl or naphthyl; amino, mono($C_1$–$C_4$)alkylamino, di($C_1$–$C_4$)alkylamino, phenylamino, mono- or di-($C_1$–$C_4$)alkyl substituted phenylamino, mono- or di-($C_1$–$C_4$)alkoxy substituted phenylamino, diphenylamino, mono- or di-($C_1$–$C_4$)alkyl substituted diphenylamino, mono- or di-($C_1$–$C_4$)alkoxy substituted diphenylamino, morpholino, piperidino, dicyclohexylamino, pyrrolidyl, or the group —OCH($R_4$)Z; said aryl substituents being selected from the group consisting of $C_1$–$C_4$ alkyl, $C_1$–$C_4$ alkoxy, $C_3$–$C_5$ cycloalkyl, phenyl($C_1$–$C_4$)alkyl, amino, mono($C_1$–$C_4$) alkylamino, di($C_1$–$C_4$)alkylamino, dicyclohexylamino, diphenylamino, piperidino, morpholino, pyrrolidyl, bromo, chloro, fluoro, phenyl and naphthyl; Z is —CN, chloro, fluoro or —C(O)$R_8$; $R_4$ is hydrogen or $C_1$–$C_4$ alkyl; and $R_8$ is hydrogen, $C_1$–$C_4$ alkyl or $C_1$–$C_4$ alkoxy;

(b) $R_2$ is selected from the group, —C(O)W, wherein: W is hydrogen, hydroxy, $C_1$–$C_4$ alkyl; the unsubstituted, mono- or di-substituted aryl groups, phenyl or naphthyl; the group —OCH($R_4$)Z; —O$R_5$, or —N($R_6$)($R_7$); or an unsubstituted, mono-substituted or di-substituted heterocyclic ring selected from the group consisting of 1-indolinyl, morpholino, thiomorpholino, piperidino, 1-pyrrolidyl, 1-imidazolidyl, 2-imidazolin-1-yl, pyrazolidyl, pyrazolinyl and 1-piperazinyl; $R_5$ is $C_1$–$C_4$ alkyl, allyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, ($C_1$–$C_4$)alkoxy ($C_2$–$C_3$)alkyl, $C_1$–$C_4$ haloalkyl; or the unsubstituted, mono- or di-substituted aryl groups, phenyl or naphthyl; said halo substituent being chloro or fluoro; and $R_6$ and $R_7$ are each selected from the group consisting of hydrogen, $C_1$–$C_4$ alkyl, $C_5$–$C_6$ cycloalkyl, phenyl, mono-substituted phenyl and di-substituted phenyl; each of said phenyl, aryl, naphthyl and heterocyclic ring substituents being $C_1$–$C_4$ alkyl or $C_1$–$C_4$ alkoxy;

(c) each $R_3$ is selected from $C_1$–$C_4$ alkyl, $C_1$–$C_4$ alkoxy, $C_3$–$C_6$ cycloalkyl, phenyl, mono- or di-substituted phenyl; said phenyl substituents being $C_1$–$C_4$ alkyl or $C_1$–$C_4$ alkoxy and n is selected from the integers 0, 1 or 2; and (d) B and B' are each selected from the group consisting of:
  (i) phenyl, mono-substituted phenyl, and di-substituted phenyl;
  (ii) the unsubstituted, mono-, and di-substituted aromatic heterocyclic groups furanyl, benzofuran-2-yl, thienyl, benzothien-2-yl and dibenzofuranyl; said phenyl and aromatic heterocyclic substituents in (d)(i) and (ii) being selected from the group consisting of hydroxy, phenyl($C_1$–$C_4$)alkyl, amino, mono ($C_1$–$C_3$)alkylamino, di($C_1$–$C_3$)alkylamino, piperidino, morpholino, $C_1$–$C_3$ alkyl, $C_1$–$C_3$ chloroalkyl, $C_1$–$C_3$ fluoroalkyl, $C_1$–$C_3$ alkoxy, mono ($C_1$–$C_3$)alkoxy($C_1$–$C_3$)alkyl, fluoro and chloro;
  (iii) the groups represented by the following graphic formulae:

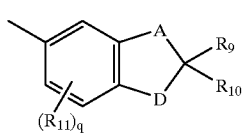 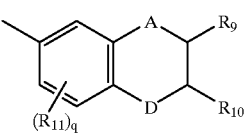

wherein A is carbon and D is oxygen, $R_{11}$ is $C_1$–$C_3$ alkyl or $C_1$–$C_3$ alkoxy, $R_9$ and $R_{10}$ are each hydrogen or $C_1$–$C_3$ alkyl; and q is the integer 0 or 1;
  (iv) $C_1$–$C_4$ alkyl; and
  (v) the group represented by the following graphic formula:

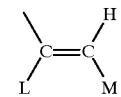

wherein L is hydrogen or methyl and M is phenyl or mono-substituted phenyl; said phenyl substituent being selected from the group consisting of $C_1$–$C_3$ alkyl, $C_1$–$C_3$ alkoxy, and fluoro; or
  (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings; each of said fluoren-9-xylidene substituents being selected from the group consisting of $C_1$–$C_3$ alkyl, $C_1$–$C_3$ alkoxy, fluoro and chloro.

3. The naphthopyran of claim 2 wherein:

(a) $R_1$ is selected from hydroxy, $C_1$–$C_3$ alkoxy; an unsubstituted, mono- or di-substituted phenyl; amino, mono($C_1$–$C_3$)alkylamino, di($C_1$–$C_3$)alkylamino, morpholino, piperidino, pyrrolidyl, or the group —OCH($R_4$)Z; said phenyl substituents being selected from the group consisting of $C_1$–$C_3$ alkyl, $C_1$–$C_3$ alkoxy, phenyl($C_1$–$C_3$)alkyl, amino, mono($C_1$–$C_3$) alkylamino, di($C_1$–$C_3$)alkylamino, piperidino, morpholino, pyrrolidyl, bromo, chloro, fluoro, phenyl and naphthyl; Z is —CN, chloro, fluoro or —C(O)$R_8$; $R_4$ is hydrogen or $C_1$–$C_3$ alkyl; and $R_8$ is hydrogen, $C_1$–$C_3$ alkyl or $C_1$–$C_3$ alkoxy;

(b) $R_2$ is selected from the group, —C(O)W, wherein: W is hydrogen, hydroxy, $C_1$–$C_3$ alkyl, phenyl, mono- or di-substituted phenyl; the group —OCH($R_4$)Z, —O$R_5$, or —N($R_6$)($R_7$); or an unsubstituted, mono-substituted or di-substituted heterocyclic ring selected from the group consisting of 1-indolinyl, morpholino, piperidino, and 1-pyrrolidyl; $R_5$ is $C_1$–$C_3$ alkyl, allyl, phenyl($C_1$–$C_2$)alkyl, mono($C_1$–$C_3$)alkyl substituted phenyl($C_1$–$C_2$)alkyl, mono($C_1$–$C_3$)alkoxy substituted phenyl($C_1$–$C_2$)alkyl, ($C_1$–$C_3$)alkoxy($C_2$–$C_3$)alkyl, $C_1$–$C_3$ haloalkyl, phenyl, mono- or di-substituted phenyl; said halo substituent being chloro or fluoro; and $R_6$ and $R_7$ are each selected from the group consisting of hydrogen, $C_1$–$C_3$ alkyl, phenyl, mono-substituted phenyl and di-substituted phenyl; each of said phenyl and heterocyclic ring substituents being $C_1$–$C_3$ alkyl or $C_1$–$C_3$ alkoxy;

(c) $R_3$ is selected from $C_1$–$C_3$ alkyl, $C_1$–$C_3$ alkoxy, $C_3$–$C_5$ cycloalkyl, phenyl, mono- or di-substituted phenyl; said phenyl substituents being $C_1$–$C_3$ alkyl or $C_1$–$C_3$ alkoxy and n is selected from the integers 0 or 1; and (d) B and B' are each selected from the group consisting of phenyl, mono-, and di-substituted phenyl; unsubstituted, mono-, and di-substituted aromatic heterocyclic groups furanyl, benzofuran-2-yl, thienyl, and benzothien-2-yl; each of said phenyl and aromatic heterocyclic substituents being selected from the group consisting of hydroxy, phenyl($C_1$–$C_3$)alkyl, $C_1$–$C_3$ alkyl, $C_1$–$C_3$ alkoxy, fluoro and chloro; and the group represented by the following graphic formula:

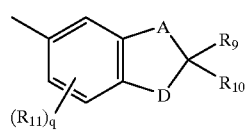

wherein A is carbon and D is oxygen, $R_{11}$ is $C_1$–$C_3$ alkyl or $C_1$–$C_3$ alkoxy, $R_9$ and $R_{10}$ are each hydrogen or $C_1$–$C_3$ alkyl, and q is the integer 0 or 1; or B and B' taken together form fluoren-9-ylidene, adamantylidene, bornylidene, norbornylidene, or bicyclo(3.3.1)nonan-9-ylidene.

4. A naphthopyran compound selected from the group consisting of:

(a) 2,2-phenyl-5-hydroxy-6-carboethoxy-2H-naphtho[1,2-b]pyran;

(b) 2,2-phenyl-5-methoxy-6-carboethoxy-2H-naphtho[1,2-b]pyran;

(c) 2,2-phenyl-5-hydroxy-6-morpholinocarbonyl-2H-naphtho[1,2-b]pyran;

(d) 2,2-phenyl-5-morpholino-6-carboethoxy-2H-naphtho[1,2-b]pyran;

(e) 2,2,5-triphenyl-6-carboethoxy-2H-naphtho[1,2-b]pyran;

(f) 2-(4-methoxyphenyl)-2-(4-morpholinophenyl)-5-hydroxy-6-carboethoxy-2H-naphtho[1,2-b]pyran;

(g) 2,2-diphenyl-5-hydroxy-6-carbomethoxy-9-methoxy-2H-naphtho[1,2-b]pyran;

(h) 2-(4-methoxyphenyl)-2-phenyl-5-morpholino-6-carbomethoxy-9-methoxy-2H-naphtho[1,2-b]pyran; and (i) 2-(4-methoxyphenyl)-2-phenyl-5-morpholino-6-carbomethoxy-9-methyl-2H-naphtho[1,2-b]pyran.

* * * * *

UNITED STATES PATENT AND TRADEMARK OFFICE
CERTIFICATE OF CORRECTION

PATENT NO. : 6,353,102 B1
DATED : March 5, 2002
INVENTOR(S) : Kumar

It is certified that error appears in the above-identified patent and that said Letters Patent is hereby corrected as shown below:

<u>Column 19,</u>
Line 60, "$(C_1-C_6)$alkyl, mono– and di $(C_1-C_6)$alkylaryl" should be -- $(C_1-C_6)$alkyl, mono– and di$(C_1-C_6)$alkylaryl --.

Signed and Sealed this

Twenty-fifth Day of June, 2002

*Attest:*

*Attesting Officer*

JAMES E. ROGAN
*Director of the United States Patent and Trademark Office*